(12) United States Patent
Blake, III

(10) Patent No.: US 6,258,101 B1
(45) Date of Patent: Jul. 10, 2001

(54) INSTRUMENT FOR DEPLOYING SURGICAL DEVICES

(75) Inventor: Joseph W Blake, III, New Canaan, CT (US)

(73) Assignee: Lacey Manufacturing Company, Inc., Bridgeport, CT (US)

( * ) Notice: Subject to any disclaimer, the term of this patent is extended or adjusted under 35 U.S.C. 154(b) by 0 days.

(21) Appl. No.: 09/535,942

(22) Filed: Mar. 24, 2000

(51) Int. Cl.⁷ ..................................................... A61B 17/24
(52) U.S. Cl. .............................................................. 606/113
(58) Field of Search .................................. 606/108, 110, 606/113, 114, 127

(56) References Cited

U.S. PATENT DOCUMENTS

| | | | |
|---|---|---|---|
| 4,619,260 | * 10/1986 | Magill et al. | 606/114 |
| 5,147,379 | * 9/1992 | Sabbaghian et al. | 606/108 |
| 5,176,677 | * 1/1993 | Wuchinich | 606/46 |
| 5,281,220 | * 1/1994 | Blake, III | 606/113 |
| 5,456,689 | * 10/1995 | Kresch et al. | 606/180 |
| 5,782,834 | * 7/1998 | Lucey et al. | 606/22 |
| 5,980,510 | * 11/1999 | Tsonton et al. | 606/1 |

* cited by examiner

Primary Examiner—Jeffrey A. Smith
Assistant Examiner—Eduardo C. Robert
(74) Attorney, Agent, or Firm—Patrick J. Walsh

(57) ABSTRACT

A surgical instrument for the deployment of medical devices such as wires and snares wherein one hand manipulates a device including advancing, opening, rotating, closing and retracting.

6 Claims, 2 Drawing Sheets

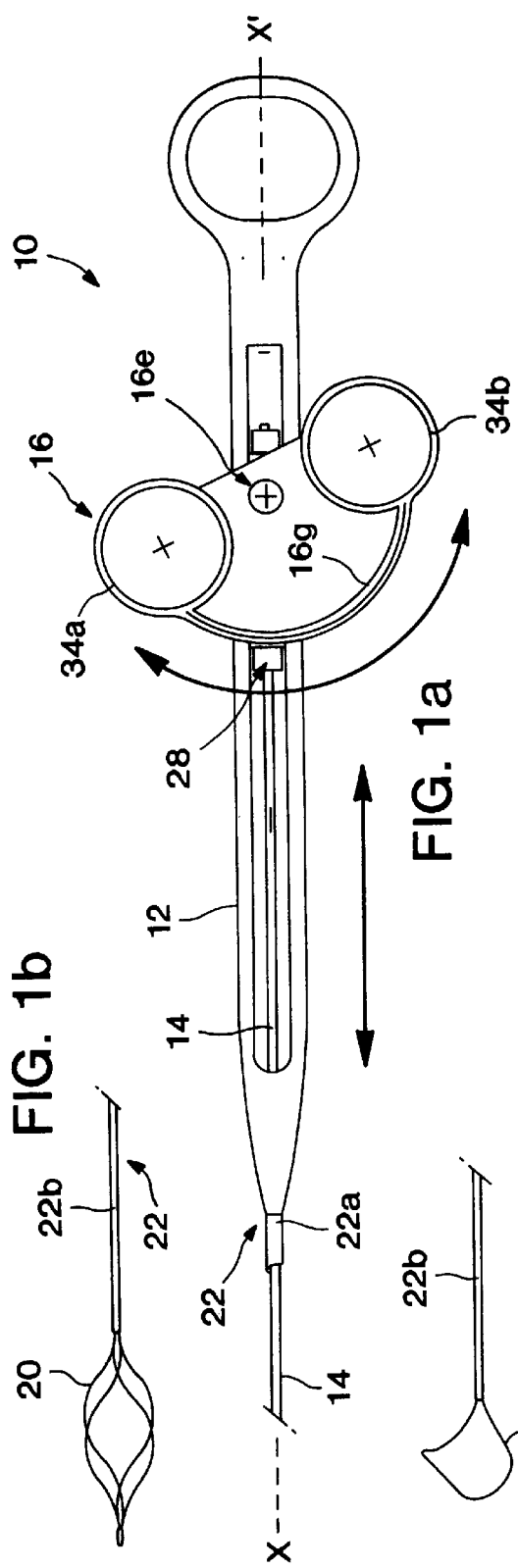
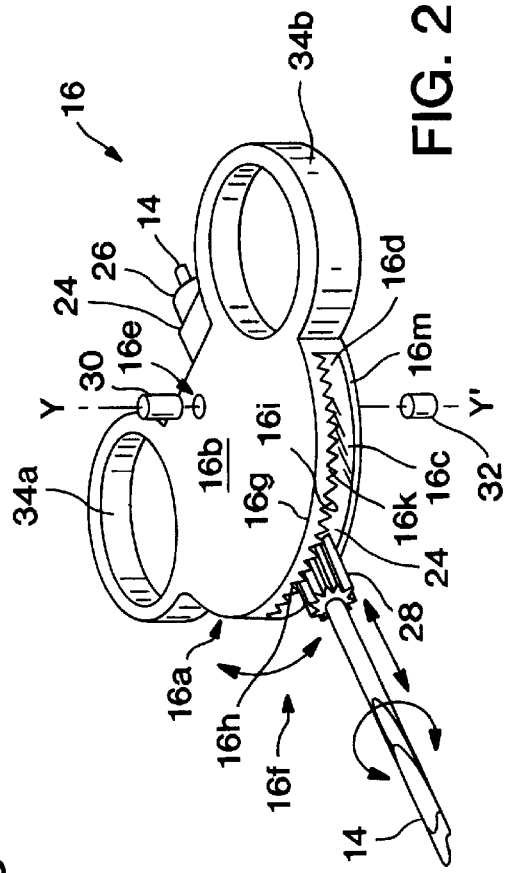

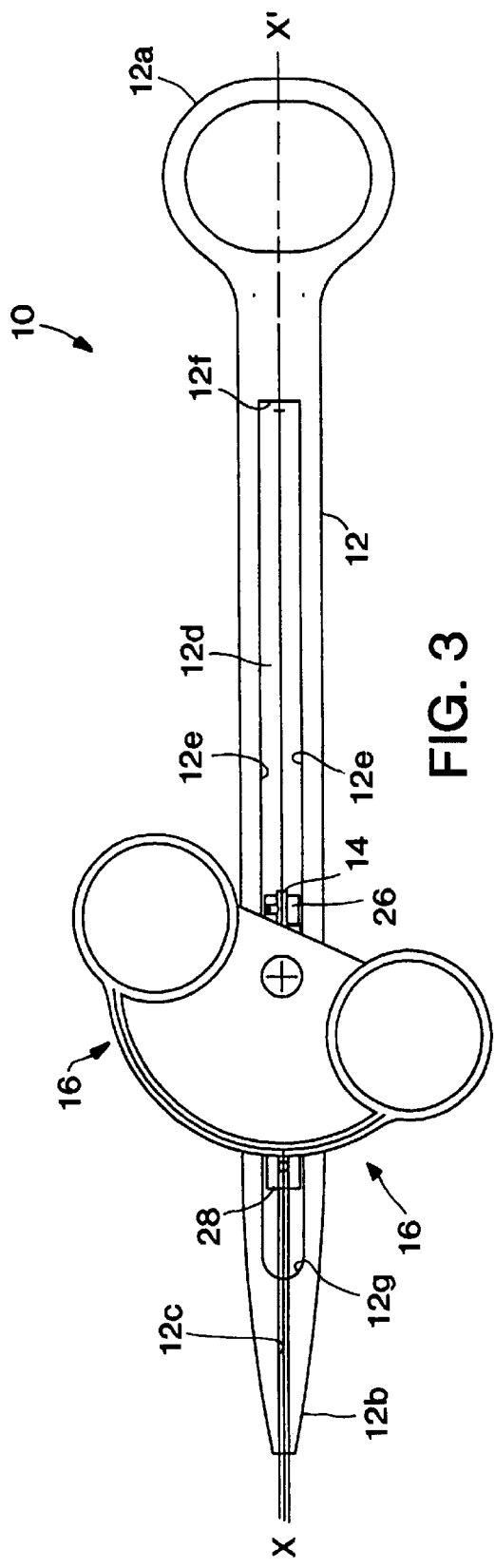
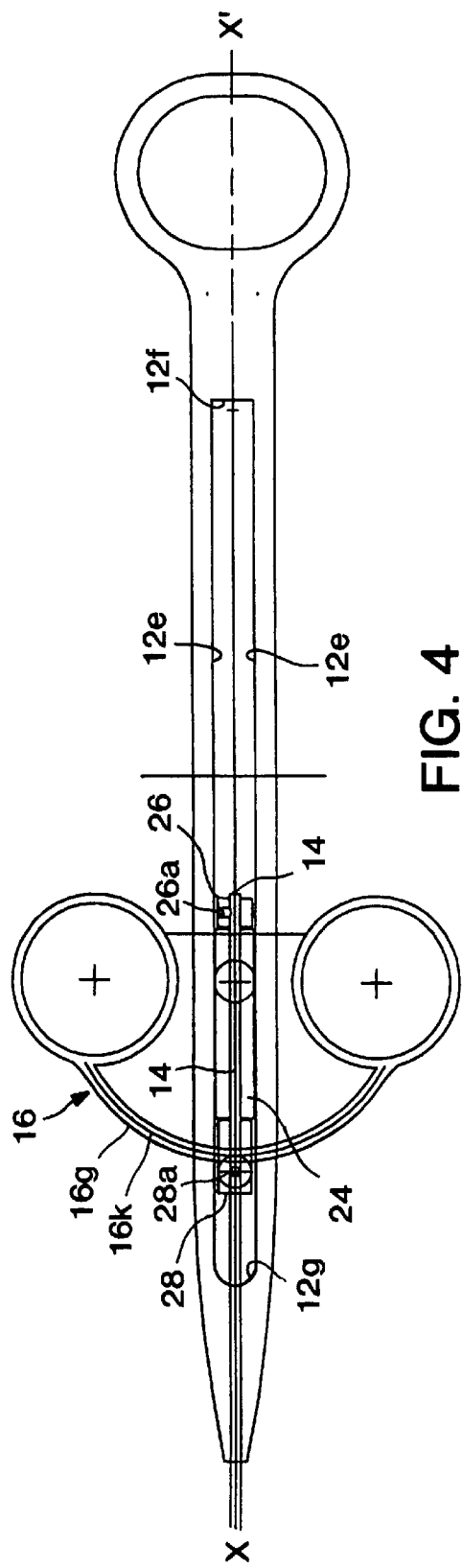

INSTRUMENT FOR DEPLOYING SURGICAL DEVICES

BACKGROUND OF THE INVENTION

The present invention relates surgical instruments and particularly to an instrument for deploying devices such as surgical wire snares and wire baskets in procedures for removal of polyps in the colon, for the retrieval of polyps after polypectomy, and for endoscopic removal of gall stones, stents or foreign bodies. The instrument is useful in a variety of applications wherein a device is manipulated through reciprocal and rotary motions by an output shaft forming part of the instrument. In particular applications, the instrument is useful for imparting reciprocating and rotary motion to snares and baskets used in surgery which are specified for the purpose of illustrating and describing the invention.

Wire snares and baskets comprise a sheath usually of Teflon encasing a wire passing through the sheath and extending from both ends thereof. The near end of the sheath is secured to an instrument for moving the wire back and forth in the sheath so as to open and close a snare or basket formed at the far end of the wire beyond the far end of the sheath. An instrument also orients the snare or basket by rotation of a wire within its sheath. In deploying snares and baskets in a surgical procedure, a hand-held instrument is used to orient, to open and to close snare or basket for a specific task.

SUMMARY OF THE INVENTION

The present invention provides a new and improved instrument for the deployment of surgical devices such as wires and snares wherein one hand manipulates a device including advancing, rotating, and retracting the device to advance the device to an operating site, to rotate for orientation as necessary, and to open and close a wire or snare to accomplish a specific task in a surgical procedure.

In a preferred embodiment, the instrument includes an elongate frame with rotatable output shaft within a sheath for deploying a surgical device such as a snare or basket and the like. The frame is in assembly with a finger carriage which is slidably and pivotally mounted on the frame and which includes a mechanism for rotating the output shaft. A thumb finger hole at the top of the frame and finger holes in the finger carriage provide for manipulation of the instrument in one hand to accomplish advance and retraction of the output shaft and basket or snare by linear sliding of the finger carriage with respect to the frame, and rotation of the output shaft by pivoting the carriage side to side with respect to the direction of linear motion. The instrument mechanism is arranged so that the output shaft can be rotated in all positions along the linear advance-retract excursion of the finger carriage and output shaft.

A surgical instrument according to the invention provides simultaneous rotation and reciprocation of an output shaft, with smooth and low operational force, and with precise manipulation of a surgical device with one hand. For purposes of illustration and specification, the instrument according to the invention is described with particular reference to surgical snares and baskets. This is done with an understanding that the instrument has utility in both reciprocating and rotating an output shaft and that the shaft and its movement are useful with other devices than baskets and snares.

OBJECTS OF THE INVENTION

An object of the invention is to provide a new and improved instrument for deploying devices in medical procedures.

Another object of the invention is to provide an instrument for one hand deployment of medical devices with simultaneous rotary and reciprocal movement.

Another object of the invention is to provide an instrument for manipulating wire baskets and snares having elongate frame with thumb hole, output shaft carried by the frame, and movable finger carriage mounted on the frame for simultaneous rotary and reciprocating manipulation of the output shaft with wire and basket.

Other and further objects of the invention will become apparent with an understanding of the following detailed description of the invention or upon employment of the invention in practice.

BRIEF DESCRIPTION OF THE DRAWING

A preferred embodiment of the invention has been chosen for detailed description to enable those having ordinary skill in the art to which the invention appertains to readily understand how to construct and use the invention and is shown in the accompanying drawing in which:

FIG. 1a is a plan view of a surgical instrument according to the invention.

FIG. 1b is a plan view of a wire basket and sheath for use with the instrument of FIG. 1a.

FIG. 1c is a plan view of a wire snare and sheath for use with the instrument of FIG. 1a.

FIG. 2 is a perspective view of a finger carriage in assembly with output shaft of the instrument of FIG. 1.

FIG. 3 is a plan view of a surgical instrument according to the invention showing the finger carriage at forward point of reciprocal excursion.

FIG. 4 is a plan view of a surgical instrument of FIG. 1 illustrating interior components of the finger carriage and their connection to the output shaft.

DETAILED DESCRIPTION OF THE PREFERRED EMBODIMENT

Referring to the drawing, a surgical instrument 10 according to the invention comprises an elongate frame 12, an output shaft 14, and a finger carriage 16.

The output shaft 14 represents the wire component of a wire snare 18 or basket 20 with the shaft being encased and freely rotatable within a flexible sheath 22. In some applications, the output shaft is the wire component of a wire snare or basket, while in other applications the output shaft may be connected to a snare or basket wire. In this description, the output shaft is regarded as the wire.

The wire 14 passes through the sheath 22 (shown truncated in FIG. 1a) with the near end 22a of the sheath affixed to the instrument frame 12 so that the instrument holds the sheath stationary as the instrument finger carriage 16 reciprocates and rotates the shaft within the sheath. The far end 22b of sheaths with wire basket 20 and snare 18 are shown in FIGS. 1b and 1c. The basket and snare are opened and closed as the instrument reciprocates the output shaft or wire, and are oriented as desired as the instrument rotates the shaft.

The frame 12 (FIGS. 3, 4) comprises a body disposed along axis x-x' with enlarged finger opening 12a at its head end, and a tapered output end 12b where the output shaft extends from the instrument through an inner passage or bore 12c. The body further includes a central slot 12d extending substantially the full length thereof along axis x-x' defined by side walls 12e and end walls 12f-g.

The central slot 12*d* receives a sliding block 24 (FIG. 4) for reciprocating movement within the full length of the slot from retracted position (FIG. 1*a*) and advanced position (FIG. 4). The output shaft 14 passes through the sliding block and the near end of the shaft receives a retaining lug 26 for holding the shaft in position at the rear face of the block. The lug is secured to the shaft by suitable means such as a set screw 26*a*. The shaft is free to rotate within the block, and the retaining lug acts as a thrust bearing for moving the shaft rearward as the block moves rearward in its slot.

A cylindrical gear 28 is mounted on the output shaft ahead of and abutting the sliding block so that sliding block 24, output shaft 14 (with retaining lug 26) and cylindrical gear 28 slide as a unit back and forth in the central slot 12*d*. The gear is secured by a set screw 28*a* (FIG. 4), for example, to the shaft so that the gear and shaft rotate as a unit. The sliding block is constrained against rotation by the slot side walls 12*e*.

The finger carriage 16 (FIG. 2) comprises a shell 16*a* of over 16*b* and under 16*c* wall members of substantially similar shape defining an open chamber 16*d* containing the subassembly of sliding block 24 with output shaft 14 and cylindrical gear 28. The finger carriage is pivotally mounted to the sliding block by over 30 and under 32 pivot pins mounted in bores 16*e* aligned on the y-y' axis.

The front face 16*f* of the shell is open and defines a segment of a circle 16*g* (concentric to the pivot axis y-y') to accommodate the cylindrical gear 28 in position in the shell opening. The upper lip 16*h* of the opening 16*i* contains a gear rack 16*k* in engagement with the shaft gear for rotation of the shaft as the carriage pivots from side to side about the pivot axis y-y'. As best shown in FIG. 4, the gear rack 16*k* intersects the midline of the shaft gear 28 so that rack and gear are always engaged.

The lower lip 16*m* (FIG. 2) of the opening defines a plane edge engaging the underside of the cylindrical gear 28 maintaining the gear in engagement with its driving rack. The gear rolls over the lower lip surface through the full excursion of the carriage about the y-y' pivot axis.

The carriage further includes integral finger holes 34*a*–*b* on either side of the long axis x-x' for receiving index and middle fingers for rotating the carriage.

In use, the instrument is held by thumb and first two fingers in position in thumb, index finger and middle finger holes. By advancing and retracting the index and middle fingers, the carriage slides down and back along the central slot. This reciprocating movement opens and closes a wire snare of basket.

By rotating the carriage to the right or left, the output shaft rotates. Rotation of the output shaft enables orientation of the snare or basket as desired.

By reason of the design of the instrument, a user is able simultaneously to reciprocate and rotate the output shaft and its snare or basket.

Various changes may be made to the structure embodying the principles of the invention. The foregoing embodiments are set forth in an illustrative and not in a limiting sense. The scope of the invention is defined by the claims appended hereto.

I claim:

1. An instrument for deploying surgical devices fitted to an output shaft, the instrument comprising an elongate frame, a carriage mounted on the frame for reciprocal movement along the frame and for pivoting movement from side to side of the frame, the carriage having means on each side thereof for pivoting the carriage, an output shaft connected to the carriage, and the carriage having means for simultaneously reciprocating and rotating the output shaft with respect to the frame.

2. An instrument for deploying surgical devices including snares and baskets, the instrument comprising an elongate frame, a sheath affixed to the frame, means defining a path along the frame, a carriage mounted on the frame for reciprocal movement along the path and for pivoting movement from side to side of the path, the carriage having finger receiving means on each side thereof for imparting pivoting movement to the carriage, a wire rotatably connected to the carriage and extending through the sheath, and the carriage having means for reciprocating the wire along the path, and the carriage further having means for rotating the wire with respect to the sheath.

3. An instrument for deploying surgical snares and baskets, the instrument comprising a frame having a longitudinal axis, the frame having a slot along the axis defining a path for linear reciprocal movement, a sheath affixed to the frame, a carriage mounted in the slot for reciprocal movement along the frame and for pivoting movement from side to side of the frame on an axis normal to the longitudinal axis, the carriage having means on each side of the longitudinal axis for manually pivoting the carriage, a wire connected to the carriage and extending through the sheath, and the carriage having a mechanism for simultaneously reciprocating and rotating the wire with respect to the sheath.

4. An instrument for deploying surgical devices by means of a reciprocating and rotating output shaft, the instrument comprising a frame having a longitudinal axis, a sheath affixed to the frame, the frame having a slot along the axis defining a path for linear reciprocal movement, a sliding block situated in the slot for movement along said path, an output shaft passing through the sheath and connected to the sliding block for reciprocal movement along said path, a carriage pivotally mounted to the sliding block for reciprocal movement with the sliding block and for pivoting movement from side to side of the frame, and the carriage having a mechanism for rotating the output shaft whereby carriage simultaneously reciprocates and rotates the output shaft with respect to the frame.

5. An instrument as defined in claim 4 in which the mechanism for rotating the output shaft comprises a gear rack on the carriage and a gear fitted to the output shaft wherein side-to-side movement of the carriage rotates the output shaft.

6. An instrument for deploying surgical snares having a wire and sheath, the instrument comprising a frame having a longitudinal axis and near and far ends, a thumb finger hole at the near end of the frame, a sheath affixed the far end of the frame, the frame having a central slot along the axis defining a path for linear reciprocal movement, a sliding block situated in the slot for linear reciprocal movement along said path, an output shaft passing through the sheath and connected to the sliding block for reciprocal movement along said path, a carriage pivotally mounted to the sliding block for reciprocal movement with the sliding block and for pivoting movement from side to side of the longitudinal axis, the carriage having an arcuate gear rack, a cylindrical gear secured to the output shaft in engagement with the gear rack for rotating the output shaft, the carriage having finger holes disposed on either side of the longitudinal axis whereby one hand moves the carriage simultaneously to reciprocate and rotate the output shaft.

* * * * *